(12) United States Patent
Kazantsev et al.

(10) Patent No.: US 12,150,850 B2
(45) Date of Patent: Nov. 26, 2024

(54) TENSION-FREE TITANIUM METAL KNITTED FABRIC FOR SURGICALLY SHAPING SOFT TISSUES

(71) Applicant: Titanium Textiles AG, Bentwische (DE)

(72) Inventors: Anton Anatolevich Kazantsev, g. Ekaterinburg (RU); Ajrat Auhatovich Yusupov, Sverdlovskaya oblast (RU); Alexandr Ivanovich Alehin, Moscow (RU); Vladimir Andreevich Zavaruev, Moscow (RU)

(73) Assignee: TITANIUM TEXTILES AG, Bentwisch (DE)

( * ) Notice: Subject to any disclaimer, the term of this patent is extended or adjusted under 35 U.S.C. 154(b) by 902 days.

(21) Appl. No.: 16/977,245

(22) PCT Filed: Mar. 1, 2018

(86) PCT No.: PCT/RU2018/000118
§ 371 (c)(1),
(2) Date: Sep. 1, 2020

(87) PCT Pub. No.: WO2019/168425
PCT Pub. Date: Sep. 6, 2019

(65) Prior Publication Data
US 2021/0038360 A1    Feb. 11, 2021

(51) Int. Cl.
*A61F 2/00* (2006.01)
*A61L 27/06* (2006.01)
(Continued)

(52) U.S. Cl.
CPC ............ *A61F 2/0063* (2013.01); *A61L 27/06* (2013.01); *A61L 27/56* (2013.01); *D04B 21/20* (2013.01);
(Continued)

(58) Field of Classification Search
CPC .... A61F 2/0045; A61F 2/0054; A61F 2/0059; A61F 2/0063; A61F 2002/0068; A61L 27/06; D10B 2101/20
See application file for complete search history.

(56) References Cited

U.S. PATENT DOCUMENTS

| | | |
|---|---|---|
| 6,214,049 B1 | 4/2001 | Gayer et al. |
| 6,709,379 B1 | 3/2004 | Brandau et al. |
| (Continued) | | |

FOREIGN PATENT DOCUMENTS

| | | |
|---|---|---|
| CN | 101766539 A | 7/2010 |
| CN | 101766541 A | 7/2010 |
| (Continued) | | |

OTHER PUBLICATIONS

Pivkina, Svetlana Ivanovna, "Development of Technology of Knitted Fabrics and Products Made of Titanium Threads for Endoprostheses," Dissertations for the degree of Candidate of Technical Sciences, Russian State University named after A.N. Kosygin (Technologies. Design. Art), Moscow, 2017, 226 pages.
(Continued)

*Primary Examiner* — Thaddeus B Cox
(74) *Attorney, Agent, or Firm* — MUNCY, GEISSLER, OLDS & LOWE, P.C.

(57) ABSTRACT

The invention relates to the fields of medicine and medical technology and is directed toward improving the technical properties of mesh implants used for delicately surgically shaping thin anatomical structures: eyelids, cornea, etc. A tension-free titanium metal warp knit fabric for surgically shaping soft tissues is a mesh fabric made of titanium threads bent to form interconnected loops, wherein the titanium threads have a contoured surface. The technical result is a decrease in the elasticity and an increase in the plasticity of the material, making it possible to incorporate said material into thin anatomical structures without risk of (Continued)

trauma, while improving the formation of connective tissue, reducing wound discharge, shortening healing times, and reducing the rate of complications, thus enabling more rapid recovery of patients.

8 Claims, 2 Drawing Sheets

(51) Int. Cl.
  *A61L 27/56* (2006.01)
  *D04B 21/20* (2006.01)
(52) U.S. Cl.
  CPC .. *A61F 2002/0068* (2013.01); *D10B 2101/20* (2013.01); *D10B 2509/00* (2013.01)

(56) References Cited

U.S. PATENT DOCUMENTS

| | | |
|---|---|---|
| 6,911,046 B2 | 6/2005 | Schulter |
| 9,732,321 B2 | 8/2017 | Bassett et al. |
| 2003/0068595 A1 | 4/2003 | Pitnick et al. |
| 2006/0008773 A1 | 1/2006 | Liao |
| 2007/0154621 A1 | 7/2007 | Raad |
| 2008/0274671 A1 | 11/2008 | O'Donoghue et al. |
| 2008/0294271 A1 | 11/2008 | Bjursten et al. |
| 2008/0318044 A1 | 12/2008 | Tian et al. |
| 2009/0030504 A1 | 1/2009 | Weber et al. |
| 2009/0112310 A1 | 4/2009 | Zhang |
| 2009/0220561 A1 | 9/2009 | Jin et al. |
| 2010/0303722 A1 | 12/2010 | Jin et al. |
| 2010/0311615 A1 | 12/2010 | Qu et al. |
| 2011/0085968 A1 | 4/2011 | Jin et al. |
| 2011/0125263 A1 | 5/2011 | Webster et al. |
| 2011/0159070 A1 | 6/2011 | Jin et al. |
| 2014/0371687 A1 | 12/2014 | Mendelsohn et al. |
| 2016/0220496 A1 | 8/2016 | Roorda |
| 2016/0220730 A1 | 8/2016 | Procter et al. |
| 2017/0274089 A1 | 9/2017 | Mendelsohn et al. |
| 2019/0358021 A1* | 11/2019 | Kubo ................ A61B 17/0057 |

FOREIGN PATENT DOCUMENTS

| | | |
|---|---|---|
| CN | 101785880 A | 7/2010 |
| CN | 102058904 A | 5/2011 |
| CN | 103143068 A | 6/2013 |
| CN | 103357070 A | 10/2013 |
| CN | 104274862 A | 1/2015 |
| CN | 104826159 A | 8/2015 |
| CN | 104941002 A | 9/2015 |
| CN | 105935317 A | 9/2016 |
| CN | 106110391 A | 11/2016 |
| CN | 106377495 A | 2/2017 |
| CN | 106390207 A | 2/2017 |
| CN | 106729964 A | 5/2017 |
| CN | 206198351 U | 5/2017 |
| CN | 107569716 A | 1/2018 |
| DE | 10040590 C2 | 7/2002 |
| DE | 10247397 B3 | 1/2004 |
| DE | 10311990 B4 | 4/2006 |
| DE | 202006015415 U1 | 11/2006 |
| DE | 202006015416 U1 | 11/2006 |
| DE | 10219853 B4 | 8/2009 |
| DE | 102008018202 A1 | 10/2009 |
| DE | 202013006283 U1 | 4/2014 |
| DE | 202014102531 U1 | 7/2014 |
| DE | 202015102114 U1 | 5/2015 |
| DE | 102008037204 B4 | 1/2016 |
| DE | 10301850 B4 | 5/2017 |
| DE | 102015107291 B4 | 6/2017 |
| DE | 102016107791 B4 | 3/2018 |
| EP | 0880946 A1 | 12/1998 |
| EP | 0746269 B1 | 3/2000 |
| EP | 0706876 B1 | 7/2000 |
| EP | 0839221 B1 | 9/2000 |
| EP | 0773751 B1 | 10/2001 |
| EP | 0755664 B1 | 12/2002 |
| EP | 0986347 B1 | 12/2003 |
| EP | 1035808 B1 | 3/2004 |
| EP | 1309294 B1 | 7/2005 |
| EP | 1407727 B1 | 8/2005 |
| EP | 1219246 B1 | 3/2006 |
| EP | 1669032 A2 | 6/2006 |
| EP | 0788802 B1 | 7/2006 |
| EP | 1552855 A1 | 8/2008 |
| EP | 1683501 B1 | 10/2008 |
| EP | 1997521 A1 | 12/2008 |
| EP | 1629796 B1 | 3/2009 |
| EP | 2062554 A1 | 5/2009 |
| EP | 2153787 A1 | 2/2010 |
| EP | 2078512 B1 | 7/2012 |
| EP | 2567716 A1 | 3/2013 |
| EP | 1551332 B1 | 10/2013 |
| EP | 2163268 B1 | 1/2014 |
| EP | 2687188 A1 | 1/2014 |
| EP | 2764877 B1 | 4/2016 |
| EP | 1800699 B1 | 4/2017 |
| EP | 2765216 B1 | 11/2017 |
| EP | 1852135 B1 | 4/2018 |
| EP | 2714974 B1 | 6/2019 |
| JP | 2010215438 A2 | 9/2010 |
| JP | 2016534241 A | 11/2016 |
| KR | 20110113589 A | 10/2011 |
| KR | 20120120784 A | 11/2012 |
| KR | 101297814 B1 | 8/2013 |
| KR | 20140035733 A | 3/2014 |
| KR | 20160070055 A | 6/2016 |
| KR | 20200126380 A | 11/2020 |
| KR | 102459873 B1 | 10/2022 |
| KR | 102459884 B1 | 10/2022 |
| RU | 121735 U1 | 11/2012 |
| RU | 2469744 C1 | 12/2012 |
| RU | 160627 U1 | 3/2016 |
| RU | 2578359 C1 | 3/2016 |
| WO | 9930632 A1 | 6/1999 |
| WO | 0162180 A1 | 8/2001 |
| WO | 03037209 A1 | 5/2003 |
| WO | 03042440 A2 | 5/2003 |
| WO | 2005114120 A2 | 12/2005 |
| WO | 2006053044 A1 | 5/2006 |
| WO | 2007030274 A2 | 3/2007 |
| WO | 2008040408 A1 | 4/2008 |
| WO | 2008040409 A1 | 4/2008 |
| WO | 09032956 A1 | 3/2009 |
| WO | 10016622 A1 | 2/2010 |
| WO | 2010097635 A1 | 9/2010 |
| WO | 2010117641 A2 | 10/2010 |
| WO | 2011060177 A2 | 5/2011 |
| WO | 2011069161 A1 | 6/2011 |
| WO | 2011136824 A1 | 11/2011 |
| WO | 2012160308 A1 | 11/2012 |
| WO | 2014097603 A1 | 6/2014 |
| WO | 2014098779 A2 | 6/2014 |
| WO | 2014107601 A1 | 7/2014 |
| WO | 14148765 A1 | 9/2014 |
| WO | 2014181144 A1 | 11/2014 |
| WO | 2015010643 A1 | 1/2015 |
| WO | WO-2015017032 A1 | 2/2015 |
| WO | 2016024942 A1 | 2/2016 |
| WO | 2016140638 A1 | 9/2016 |
| WO | 16171310 A1 | 10/2016 |
| WO | 2017180318 A1 | 10/2017 |
| WO | 18107092 A1 | 6/2018 |

OTHER PUBLICATIONS

Pivkina, Svetlana Ivanovna, "Development of Technology of Knitted Fabrics and Products Made of Titanium Threads for Endoprostheses," Dissertations for the degree of Candidate of Technical Sciences, Russian State University named after A.N. Kosygin (Technologies. Design. Art), Moscow, 2017, 17 pages.

(56) References Cited

OTHER PUBLICATIONS

Notice of Allowance of KR Application No. 10-2020-7028318 dated Oct. 17, 2023 and English translation, 8 pages.
Kolpakov, A.A., Ruchkin, V.I., Kolpakova, G.I. (2010) Proceedings of the VII Conference—Current issues in herniology, Oct. 20-21, 2010, 137-140.
Kolpakov, A.A. (2011). Combined prosthesis for surgical treatment of primary ventral hernias. VIII Conference—Current issues in herniology, Nov. 1-2, 2011, 113.
Kolpakov, A.A. (2011). Clinical comparison of the results of using Prolene, nickelid titanium and titanium meshes in combined abdominal wall defect repair. VIII Conference—Current issues in herniology, Nov. 1-2, 2011, 112.
Parshikov, V. V., Samsonov, A. V., Khodak, V. A., Petrov, V. V., Romanov, R. V., Samsonov, A. A., Gradusov, V. P., Tsybusov, S. N., Baburin, A. B., & Kazantsev, A. A. (2011). Abdominal wall plasty with Titanium Silk meshes. VIII Conference—Current issues in herniology, Nov. 1-2, 2011, 157-159.
Lazovsky, S.D., Karlov, D.I., Kazantsev A.A. (2012) Case of reconstruction of the tendon of the rectus femoris muscle with titanium mesh for reinforcing plasty of soft tissues 'Titanium Silk' Demidovskaya Central District Hospital, Nizhny Tagil, Russia, NPF Temir, Yekaterinburg, Russia.
Parshikov, V. V., Samsonov, A. V., Romanov, R. V., Gradusov, V. P., Samsonov, A. A., Khodak, V. A., Petrov, V. V., Tsybusov, S. N., Baburin, A. B., Kihlyarov, P. V., & Kazantsev, A. A. (2012). The first experience of the plastics of the abdominal wall with endoprostheses from Titanium Silk. Medical Almanac, 1(20), 107-110.
Parshikov, V. V., Khodak, V. A., Petrov, V. V., Dvornikov, A. V., Mironov, A. A., Samsonov, A. A., & Romanov, R. V. (2012). Retromuscular plasty of abdominal wall using mesh. Fundamental Research, (7), 159-163.
Chernov, A. V., Irianov, Y. M., Radchenko, S. A., Chernov, V. F., & Irianova, T. Y. (2012). Studying the integration features of different biomaterials in organism soft and bone tissues. Genius of Orthopedics, 1, 97-101.
Volova, L.T., Ponomareva, J.V., & Rozenbaum, A.Y. (2012). The value of testing in cell culture for low toxicity effect detection of medical devices. Bulletin of Emergency and Restorative Medicine. 13(1), 48-51.
Limonov, A.V., Zabrodin, V.V., Valiev, E.F., Zabrodin, E.V. (2014) Application of titanium mesh endoprosthesis for allotransplantation of inguinal hernias. Medical Bulletin of the Ministry of Internal Affairs. 1(68), 49-51.
Zhuravlev, V. A., & Kazakova, A. V. (2014). Methods of Mobile Teeth Splinting in Chronic Generalized Periodontitis Treatment (Review).Problems of Dentistry, (2) 4-8.
Kazakova, A.V., & Zhuravlev, V.P. (2014). Types of root splinting of mobile teeth in the complex treatment of chronic generalized periodontitis of severe degree. Medical Science and Education of the Urals, 15(4), 137-141.
Kolpakov, A.A., & Kazantsev, A.A. (2015). Comparative analysis of the results of application of the titan silk implant and polypropylene in patients with postoperative ventral hernias. Russian Medical Journal, (13).
Parshikov, V. V., Mironov, A. A., Anikina, E. A., Zaslavskaya, M. I., Alyokhin, A. I., & Kazantsev, A. A. (2015). Prosthetic repair of the abdominal wall using light and ultra-light synthetic and titanium-containing materials in high bacterial contamination (experimental study), CTM, 7(4).
Zhuravlev, V.P., Kazakova, A.V., & Kazantsev, A.A. (2015). Suture material titanell application in surgical chronic generalized periodontitis' treatment. Medical Science and Education of the Urals, (1), 79-82.
Magomedov M.M. and Magomedbekov R.E. (2015) Features of cytokine status in patients with inguinal hernias using endoprostheses, Journal of Cytokines and Inflammation, 14(4), 45-49.
Kazakova, A. V. & Zhuravlev, V. P. (2015). The feasibility of submucosal wiring method's application in periodontal flap surgery. Dentistry for everyone, 1, 14-16.

Kazantsev, A. A., Parshikov, V. V., Shemyatovsky, K. A., Alekhin, A. I., Titarov, D. L., Kolpakov, A. A., & Osadchenko, S. V. (2016). The titanium-containing mesh as a perspective group of implants for abdominal wall repair. Hirurgiia, (4), 86-95. Doi: 10.17116/hirurgia2016486-95.
Parshikov, V. V., Mironov, A. A., Anikina, E. A., Kazantsev, A. A., Zaslavskaya, M. I., & Alyokhin, A. I. (2016). To the question about a possibility of use ultra-light titanium-containing mesh in abdominal wall repair in contaminated fields (experimental study). Hirugiia, 11, 64-70, doi: 10.17116/hirurgia20161164-70.
Ponomareva Y.V., Volova L.T., Belokonev V.I., Milyakova M.N., (2016) The role of the proteomic spectrum in predicting the biocompatibility of prosthetic materials, First All-Russian Congress of herniologists. Moscow, Oct. 27-28, 2016, 74-75.
Khodakov V.V., Zabrodin V.V., Zabrodin E.V. (2016) Evaluation of the effectiveness of inguinal hernia alloplasty with the use of titanium mesh endoprostheses. Medical Bulletin of the Ministry of Internal Affairs. 6 (85), 13-16.
Parshikov V.V., Kazantsev A.A., Mironov A.A., Zavaruev V.A., Chernikov A.N., Belayev O.F., Alyokhin A.I. (2016) Strength properties of abdominal wall in intraperitoneal and retromuscular repair using lightweight and ultra-lightweight synthetic and titanium-containing endoprostheses (experimental study). Modern technologies in medicine, 8(3), 27-36. http://dx.doi.org/10.17691/stm2016.8.3.03.
Reshetov I.V., Starceva O.I., Istranov A.L., Vorona B.N., Lyundup A.V., Gulyaev I.V., Melnikov D.V., Shtansky D.V., Sheveyko A.N., Andreev V.A. (2016). Development of a three-dimensional biocompatible matrix for tasks of reconstructive surgery. Annals of Plastic, Reconstructive and Aesthetic Surgery, (2), 85-92.
Milyakova, M. N., Ponomareva, J. V., Gribkova, O. V., Sarbayeva, N. N., Limareva, L. V., & Bogush, V. V. (2016). Functional features of macrophages during the interaction with implants for hernioplasty. Technology of Living Systems, 10(8), 84-89.
Pechetov, A.A., Esakov, Y.S., Makov, M.A., Bazyluk, A.V., & Khlan, T.N. (2017). Combined Thoracoplasty in Total Postoperative Sternum Instability after Chronic Sternomediastinitis. High Technology Medicine, 4(4), 30-35.
Parshikov, V. V., Mironov, A. A., Kazantsev, A. A., & Alyokhin, A. I. (2017). Adhesions in the abdominal cavity after non-tension plasty with ultralight synthetic plastics and titanium-containing endoprostheses. Modern technologies in medicine, 9(3), 45-54.
Nerobeev, A. I., & Kobazev, V. E. (2017). The use of titanium-containing mesh implants to eliminate ptosis of the soft tissues of the face in case of paralysis of the facial muscles. Clinical Dentistry, (2), 36-38.
Kazantsev, A. A., Tulyakov, S. S., Alekhin, A. I., Khoninov, B. V., Kazakova, A. V., Kozlov, N. A., Battaray, B., & Babichenko, I. I. (2017). Prospects for the use of polyfilament titanium suture material in traumatology. RMJ, 25(8), 533-538.
Starceva, O. I., Reshetov, I. V., Istranov, A. L., Vorona, B. N., Lyundup, A. V., Gulyaev, I. V., Melnikov, D. V., Shtansky, D. V., Sheveyko, A. N., & Andreev, V. A. (2017). Development of a three-dimensional biocompatible matrix in reconstructive surgery. Annals of Plastic, Reconstructive and Aesthetic Surgery, (1), 131-132.
Pivkina, S. I., & Kolesnikova, E. N. (2017). The knitting technology features for round-shaped integrally knitted implants made of titanium threads. In First Kosygin Readings. Kosygin State University of Russia.
Magomedov M.M., Magomedbekov R.E., Ismailov G.M. (2017) Systemic inflammatory response in alloplastic methods of inguinal hernia treatment. Journal of New Medical Technologies. Electronic edition. (2), 139-144.
Abalyan A.K., Aydemirov A.N., Mashurova E.V. (2017). First experience in using mesh endoprostheses made of Titanium Silk in the treatment of anterior abdominal wall hernias. In Proceedings of the II Congress of Herniologists, Moscow, 2017.
Alekhin, A.I., Shemyatovsky, K.A., Azimov, R.Kh., Kalinichenko, A.Yu., Glushkov, P.S., Yumatova, E.A., & Malyavko, V.A. (2017). Evaluation of the sizes and positioning of "Titanium Silk" implants using computed tomography after hernioplasty. II All-Russian Congress of Herniologists, Oct. 26-27, 2017, Moscow.

(56) References Cited

OTHER PUBLICATIONS

Parshikov, V.V., Chebotar, I.V., Anikina, E.A., Mironov, A.A., Kazantsev, A.A., & Alekhin, A.I. (2017). Biofilm process after implantation of ultra-light synthetic and titanium-containing endoprostheses under conditions of contamination with highly pathogenic microflora in experiment. II All-Russian Congress of Herniologists, Oct. 26-27, 2017, Moscow.

Kchibekov, E. A., Kokhanov, A. V., Kaliev, D. R., Kudaev, S. V., Bondarev, V. A., & Serdyukov, M. A. (2018) Features of inflammatory reaction of rats to implantation of modern mesh endoprosthesis for hernioplasty. Modern problems of science and education, (1), 61-61.

Reshetov, I. V., Starceva, O. I., Istranov, A. L., Vorona, B. N., Lyundup, A. V., Melnikov, D. V., Shtansky, D. V., & Sheveyko, A. N. (2018). Development of a 3D biocompatible composite matrix for reconstructive surgery of hollow organs and tissues. Annals of Plastic, Reconstructive and Aesthetic Surgery, (1), 99-100.

Karapetyan, G.E., & Cherepanova, T.V. (2018). Method of Surgical Correction of Defects of Front Angle Wall. Surgical Moscow Journal, 2(60), 47-51. doi: 10.17238/issn2072-3180.2018.2.47-51;

https://www.bebdental.it/ru/регенерация-кости/титановые-мембраны-t-barrier (retrieved from the internet; Wayback machine snapshots of Aug. 14, 2017 and Oct. 10, 2017).

\* cited by examiner

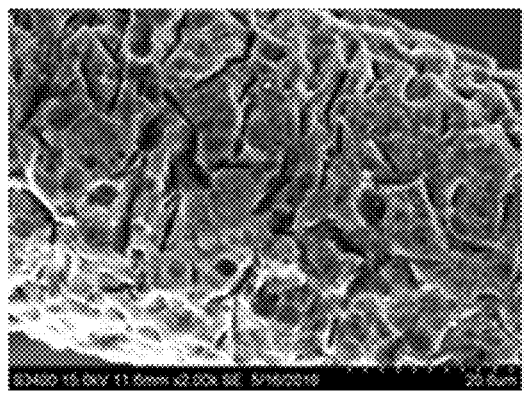
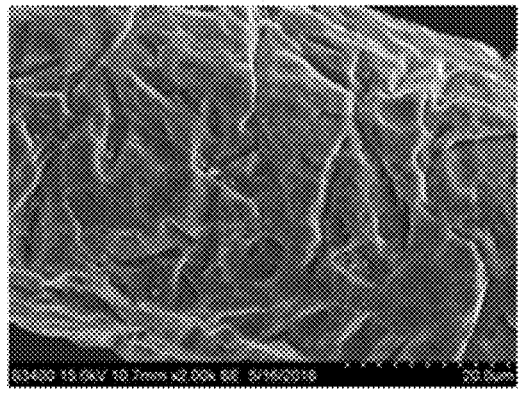
FIG. 3a					FIG. 3b
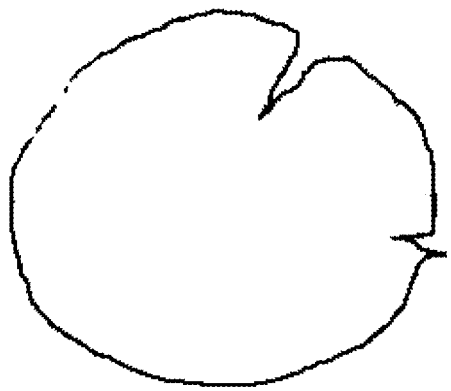
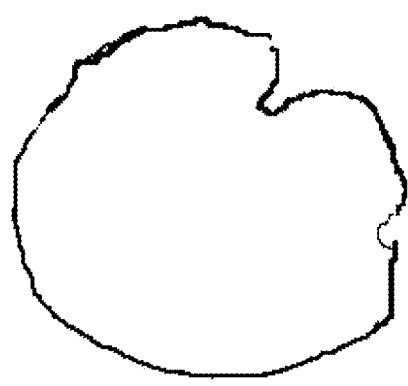
FIG. 4a					FIG. 4b

TENSION-FREE TITANIUM METAL KNITTED FABRIC FOR SURGICALLY SHAPING SOFT TISSUES

CROSS REFERENCE TO RELATED APPLICATIONS

This nonprovisional application is a U.S. national stage application of International Application No. PCT/RU2018/000118, which was filed on Mar. 1, 2018, and is herein incorporated by reference.

FIELD OF THE INVENTION

The invention relates to the fields of medicine and medical technology and is directed toward improving the technical properties of mesh endoprostheses used for delicately surgically shaping thin anatomical structures: eyelids, facial tissues, abdominal inguinal ring, etc.

STATE OF ART

A solution is known from the prior art (RU 160627 U1, publ. 27 Mar. 2016), which describes a mesh material for hernioplasty. A mesh of titanium threads with a biologically active coating is fixed on the edges with interrupted, U-shaped sutures or a continuous suture along the perimeter. If the most reliable fixation of the mesh to the tissues is needed, a second perimeter of the sutures can be applied along the edges of the hernial orifice.

A disadvantage of this solution, as well as the above, is that when fixing the mesh endoprosthesis, additional fixators are used in the form of sutures made in various ways or staples. This solution does not allow to establish quickly a strong fixation of the endoprosthesis and to ensure uniform fixation of the endoprosthesis with the entire surface thereof to the tissues of the surgical wound, while the threads do not have high plasticity and have a high risk of breakage.

A solution is known from the prior art (RU 121735 U1, publ. 10 Nov. 2012), which describes titanium metal knitted fabric for surgically shaping. The metal knitted fabric is made in the form of a mesh with threads of a titanium alloy having titanium content of at least 80%, while the mesh contains threads bent to form interconnected loops. The mesh is fixed on the edges with interrupted, U-shaped sutures or a continuous suture along the perimeter. If the most reliable fixation of the mesh to the tissues is needed, a second perimeter of the sutures can be applied along the edges of the hernial orifice. It is also possible to fix the mesh with titanium staples.

Disadvantages of native metal knitted fabric (which has not been treated by additional methods affecting the thickness of the thread) are spring properties (elasticity), which inevitably occur when the material is deformed to form wire loops, the density of which is often higher than that of a weft-knitting material. Due to the mutual tension of the wire loops, the mesh can deform, twist, form folds and put pressure on adjacent structures, causing tension of the body tissues to which it is sewn. As a result of elasticity, pressure ulcer development in the tissues, cheese-wiring of the material through the delicate structures, tearing the mesh from the suture material, wrinkling the implant, curling the edges of the material, and difficulty with expanding thereof in the surgical wound can appear. At the same time, the spring properties do not allow the material to be used when it should be placed in thin anatomical structures, such as the submucosa of the eyelids, cornea, etc., posing a risk of cheese-wiring of the material or perforating the mucous membrane with individual threads of the titanium mesh. The materials existing today do not allow to make quickly an appropriate placement of native metal knitted fabric in thin anatomical structures having a mucous membrane with a thickness of adjacent tissues less than 1 mm, as well as to provide uniform fixation thereof with the entire surface to the tissues of the surgical wound.

The claimed invention makes it possible to substantially overcome the indicated disadvantages inherent in the prototype.

DISCLOSURE OF THE INVENTION

The technical problem that the proposed technical solution solves is the development of metal knitted fabric having high plasticity and low elasticity, which reduces the risk of trauma to thin anatomical structures and allows the metal knitted fabric to be used in those fields where implants made of metal knitted fabric have not been used until now (for example, shaping of the eyelid submucosa, cornea, etc.).

The technical result is a decrease in the elasticity and an increase in the plasticity of the metal knitted fabric, making it possible to incorporate said fabric into thin anatomical structures without risk of trauma, while improving the formation of connective tissue, reducing wound discharge, shortening healing times, and reducing the rate of complications, thus enabling more rapid recovery of patients, and, as a consequence, expanding the scope of applicability of metal knitted fabric in those fields where the biological inertness of titanium and high plasticity of the material are of particular importance.

The technical result is achieved due to the fact that tension-free titanium metal knitted fabric for surgically shaping soft tissues is a mesh fabric made of titanium threads bent to form interconnected loops, wherein the titanium threads have a relief surface.

The mesh fabric is made on the basis of a weft-knitting or warp-knitting structure.

The contoured surface of the titanium thread provides a varying diameter of the titanium thread with fluctuations from 0.0025 mm.

An oxide film is applied to the surface of the contoured titanium threads.

The oxide film has a thickness of 1-3 µm.

Titanium threads are made from GRADE-5 alloy.

BRIEF DESCRIPTION OF DRAWINGS

FIG. 3a. Example of thread surface relief after chemical etching.

FIG. 3b. Example of thread surface relief after ion treatment.

FIG. 4a. Cross-section of a thread with longitudinal sharp-pointed defects before the treatment.

FIG. 4b. Cross-section of a thread with smoothed longitudinal defects after the treatment.

EMBODIMENTS OF THE INVENTION

Tension-free metal knitted fabric is a mesh fabric made of titanium threads bent to form interconnected loops, which fabric is used as endoprostheses, intended, for example, for delicately shaping soft tissues with a layer thickness of less than 1 mm above the thread (upper and lower eyelids, parietal peritoneum, etc.). Tension-free metal knitted fabric can be made of any shape and size needed for performing operations for implantation thereof.

The mesh fabric is represented by a filling-knit (thread diameter is 100-140 μm) or warp-knitted (thread diameter is 20-70 μm) mesh. Threads can be made of VT1-00, VT-1.00 wa (GRADE-1) or VT6 (GRADE-5) titanium alloys. The titanium threads used have high biological inertness and plasticity of the threads, and make it possible to avoid tissue trauma. The titanium threads have a relief surface.

Figure 1A:
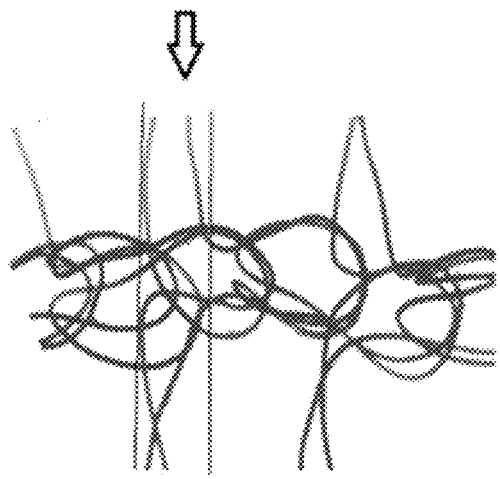
FIG. 1a. The state of the interloop range in a tension-free metal knitted fabric with relief threads.
Figure 1B:
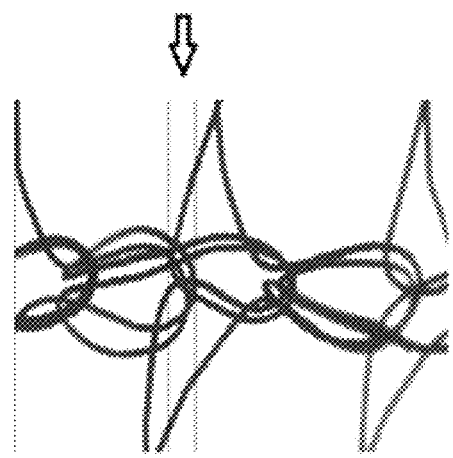
FIG. 1B. The state of the interloop range in a native metal knitted fabric with threads without relief.

Technological processes that make it possible to obtain tension-free metal knitted fabric with a relief surface of the titanium thread are: power ultrasonic treatment, chemical etching, electrochemical polishing, ion treatment, etc. These methods of treatment reduce the diameter of the titanium thread, which are already in the structure of the knitted mesh fabric, by 10-35% of the initial diameter, at the same time reducing the area of interloop contacts, thereby reducing the elastic properties and significantly increasing the plasticity of the metal knitted fabric, forming a porous structure with high adhesion to the wound surface. As a result, a "telescopic effect" is achieved: the penetration of loops and interloop floats into the area of adjacent loops, which is shown in FIG. 1a. This effect is not observed in the untreated (native) metal knitted fabric (FIG. 1B). In FIGS. 1a and 1b, arrows and straight lines indicate the interpenetration of loops and interloop floats inside the loops in one wale, wherein interpenetration in FIG. 1a is much more.

The telescopic effect and reduction of resistance in the area of interloop contacts is the main factor in the elimination of "spring" properties of the metal knitted fabric. This fact is proved by measuring the mechanical properties of the material.

Therefore, when stretching knitted meshes, there is a period of zero rigidity Z (FIG. 2), which is shown as an area on the diagram where the mesh fabric is stretched without resistance, where Z aten is zero rigidity of the tension-free metal knitted fabric with relief threads, and Z nat is zero rigidity of the native metal knitted fabric with threads without relief. When comparing native and tension-free metal knitted fabric of the same type of knitting and thread thickness, it is determined that the area of zero rigidity of the tension-free metal warp knit mesh is at least 20% bigger than that of the native material.

As a result of technological operations, the relief surface of the titanium thread is formed: chaotically spreading depressions and bumps (FIGS. 3a and 3b).

In addition, on the surface of the thread located in the structure of the tension-free mesh fabric, longitudinal sharp-pointed defects (FIG. 4a) arising from the drawing of the thread are smoothed in the process of treatment, for example, by electrochemical polishing. The smoothing of defects after the treatment is shown in FIG. 4b. Longitudinal defects, which are the concentrators of internal stress, are smoothed, therefore additional treatment harmonizes the residual stress in the thread itself and reduces the risk of the mesh fabric breakage.

The treatment also gives a varying diameter of the titanium thread with fluctuations along its length from 0.0025 mm, which also provides additional freeness of thread movement in the interloop gaps.

To further increase the plasticity, an oxide film of 1 to 3 μm thick can be applied to the surface of the tension-free metal knitted fabric. It is known that the application of titanium oxide reduces the sliding friction coefficient by about 3 times and significantly increases responsiveness of the tension-free metal knitted fabric, allowing the loops to easily slide relative to each other that positively affects the extensibility of the material. The surface oxide film reduces the friction between the knitted loops, and also the accompanying negative properties: breakage when the material is straightened, etc.

Oxide film is obtained by immersing mesh fabric made of relief threads into a galvanic bath filled with the necessary solution, with a constant current, for a certain time. Depending on the time and the selected voltage, an oxide film of 1-3 μm thick is formed on the surface of the titanium thread. In this case, the thickness of the thread itself does not increase.

High plasticity of tension-free metal knitted fabric minimizes spring properties, reduces the likelihood of biomechanical incompatibility between the tissue and the mucous membrane, and allows the material to be placed under the mucous membrane without risk of trauma. A mesh implant obtained from tension-free metal knitted fabric freely expands over the surface of the surgical wound, easily assumes and retains the given shape, and can be modeled according to the shape of the surgical wound by stretching, if necessary.

High porosity additionally increases the rate of penetration of biological fluids inside the implant, accelerates the process of implant colonization with fibroblasts and osteoblasts, and improves the biological integration of the material.

Tension-free metal knitted fabric, being in contact with the wound surface, is instantly impregnated with blood and wound discharge and exhibits pronounced adhesion to the wound surface, providing temporary self-fixation and allowing the surgeon to avoid using fixing elements: suture material, pins, micro-screws, etc. High adhesion of tension-free metal knitted fabric to the wound surface allows the titanium mesh to be placed without tension on the tissues underlying or covering the implant, preventing such a frequent complication as surgical wound dehiscence.

At the same time, the highly porous structure does not retain the wound discharge, eliminating the likelihood of fluid leaks and subsequent infection thereof.

The relief surface of the thread significantly improves the fixation of fibrin fibers thereon, thereby facilitating the attraction of fibroblasts serving as a source of newly formed connective tissue.

The main advantages of the claimed technical solution:
- obtaining a surface relief on the titanium thread;
- reducing the area of the interloop contact by reducing the diameter of the titanium thread in the structure of the finished mesh fabric, and as a consequence, the appearance of a telescopic effect;
- obtaining a varying diameter of the titanium thread with fluctuations from 0.0025 mm;
- a decrease in elasticity, an increase in plasticity, the formation of a porous structure with high adhesion to the wound surface;
- an increase in zero index of rigidity of the material.

Figure 2:
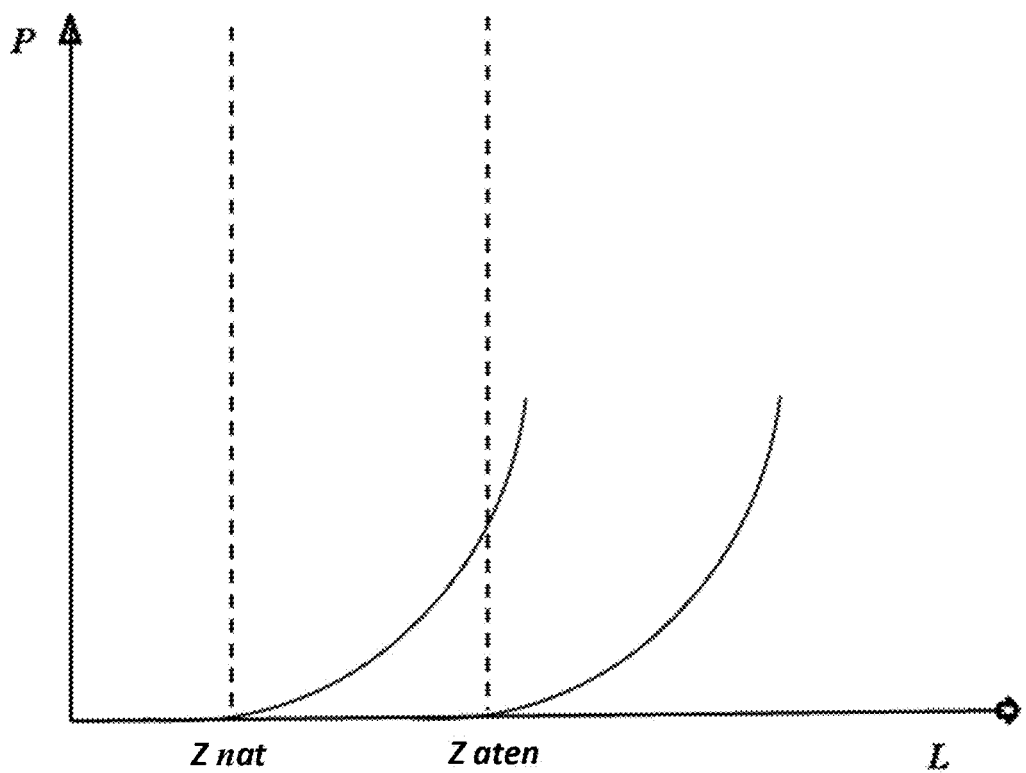
FIG. 2. Zero rigidity diagram for tensile of knitted meshes.

This indicator is measured as a percentage of the increase in the length of the mesh from the initial state to the appearance of elastic properties under tension with a force of more than 16 N/cm. At the same time, tension-free metal knitted fabric has zero index of rigidity, which is higher by 20% or more than that of native metal knitted fabric (FIG. 2).

Example 1

Endoprosthesis for keratoplasty made of tension-free metal knitted fabric with a thread diameter of 30 μm, 3×3×mm in size was obtained for three laboratory animals (rabbits, 4 months old). and was implanted using standard surgical technique. During the implanting operation, a high plasticity of the material was noted, which makes it easy to place said material in the corneal tissue. Simultaneously, a rupture of the upper eyelid with a deficit of connective tissue was simulated, where the same metal knitted fabric was used to fill it. Postoperative wound healing by primary intention. After 10 days, the animals were withdrawn from the experiment. When studying morphological changes, a whitish scar was found over the entire surface of the mesh fabric; upon microscopic examination, the structure of the postoperative scar was represented by ordered connective tissue fibers without signs of aseptic inflammation.

Example 2

Surgical interventions for implantation of the claimed tension-free titanium metal knitted fabric were performed in rats under general anesthesia with intraperitoneal Nembutal 30 mg/kg. The animals were 6 months old at the time of the intervention.

Surgical wound was formed on the anterior abdominal wall of a laboratory animal by dissecting the skin, muscles and subcutaneous adipose tissue to the peritoneum. Tension-free titanium metal knitted fabric was implanted retroperitoneally at the site of the borderline between the metal knitted fabric and the peritoneum, the thickness of which was no more than 0.5 mm. Muscle sutures, subcutaneous fat sutures, and skin sutures were applied. All animals were divided into 2 groups of 6 individuals each.

In the first group (control), meshes made of native metal knitted fabric with threads without relief were used for implantation. In the second group, the individuals were implanted with tension-free titanium metal knitted fabric with relief threads having a varying diameter along their length. Observation was carried out for 15 days. Then laboratory animals were withdrawn from the experiment.

A quick and easy installation of tension-free titanium metal knitted fabric was noted, which shortened the duration of surgery by about 15 minutes. It was noted that in the second group of animals, the restoration of the defect by primary intention proceeded without specific clinical features. During the morphological examination, a strong uniform fixation of the tension-free titanium metal knitted fabric was determined with the entire surface thereof to the tissues of the surgical wound, without displacement; there was strong connective tissue from every side of the implant. Toxic, allergic or other adverse reactions were not observed. In the first group, the installation process required far more time, which was due to edge curling and twisting of the material. Morphological examination revealed excessive scarring in the tension area. Scar adhesion was noted in the abdominal cavity. In one case, perforation of the peritoneum with elastic titanium threads and the formation of a thick infiltrate and adhesions consisting of the soldered omentum around the perforation were observed. The recovery time of the animals was 30% longer than in the main group. In one case from the control group, migration of the material was noted, and therefore a revision was required to remove it. Differences between the study groups and the control series were significant. Thus, the effectiveness of the use of the claimed tension-free titanium metal knitted fabric has been noted.

The claimed tension-free titanium metal knitted fabric has increased plasticity and low elasticity minimizing the risk of thread breakage, it is firmly and easily fixed, providing uniform fixation with the entire surface to the tissues of the surgical wound, shortening the duration of surgery, and, as a result, reducing the volume of anesthesia and trauma, resulting in a decrease in the rate of complications.

We claim:

1. A tension-free titanium metal knitted fabric for surgically shaping soft tissues, wherein said fabric is a mesh fabric made of titanium threads bent to form interconnected loops, wherein the titanium threads have a relief surface.

2. The tension-free titanium metal knitted fabric according to claim 1, wherein the mesh fabric is made on the basis of a weft-knitting structure.

3. The tension-free titanium metal knitted fabric according to claim 1, wherein the relief surface of the titanium threads provides a varying diameter of the titanium threads.

4. The tension-free titanium metal knitted fabric according to claim 3, wherein the relief surface of the titanium threads provides a varying diameter of the titanium threads with fluctuations of 0.0025 mm or more.

5. The tension-free titanium metal knitted fabric according to claim 1, wherein an oxide film is applied to the relief surface of the titanium threads.

6. The tension-free titanium metal knitted fabric according to claim 5, wherein the oxide film has a thickness of 1-3 µm.

7. The tension-free titanium metal knitted fabric according to claim 5, wherein the oxide film is applied by immersing the mesh fabric into a galvanic bath filled with a necessary solution, with a constant current.

8. The tension-free titanium metal knitted fabric according to claim 1, wherein the titanium threads are made of GRADE-1 alloy.

* * * * *